US006589933B1

United States Patent
McFadden et al.

(10) Patent No.: US 6,589,933 B1
(45) Date of Patent: Jul. 8, 2003

(54) MYXOMA CHEMOKINE BINDING PROTEIN

(75) Inventors: Grant McFadden, London (CA); Alexandra Lucas, London (CA)

(73) Assignee: Viron Therapeutics, Inc., London (CA)

(*) Notice: Subject to any disclaimer, the term of this patent is extended or adjusted under 35 U.S.C. 154(b) by 0 days.

(21) Appl. No.: 09/396,840

(22) Filed: Sep. 15, 1999

Related U.S. Application Data

(63) Continuation-in-part of application No. 09/180,877, filed on Apr. 2, 1999, now abandoned.

(51) Int. Cl.[7] .................... A61K 38/00; A61K 31/44; C12P 21/08

(52) U.S. Cl. .................... 514/2; 530/350; 530/388.23

(58) Field of Search .................... 536/23.5; 530/350, 530/388.23; 435/320.1, 325, 69.1, 7.1, 35; 424/130.1; 514/2

(56) References Cited

FOREIGN PATENT DOCUMENTS

| | | |
|---|---|---|
| WO | WO 91/16431 | 10/1991 |
| WO | WO 92/17583 | 10/1992 |
| WO | WO 96/33730 | 10/1996 |
| WO | WO 97/11714 | 4/1997 |

OTHER PUBLICATIONS

Ahuja et al., "Chemokine receptors and molecular mimicry," Immunol. Today 15:281–287 (1994).
Alcami et al., "Soluble interferon–gamma receptors encoded by poxviruses," Comp. Immunol. Microbiol. Infect. Dis. 19(4):305–317 (1996).
Alcami et al., "Vaccinia, cowpox, and camelpox viruses encode soluble gamma interferon receptors with novel broad species specificity," J. Virol. 69(8):4633–4639 (1995).
Alcami et al., "Receptors for gamma–interferon encoded by poxviruses: implications for the unknown origin of vaccinia virus," Trends Microbiol. 4(8):321–326 (1996).
Barinaga, "Viruses launch their own Star Wars," Science 258:1730–1731 (1992).
Chaudhuri et al., "Expression of the duffy antigen in K562 cells," J. Biol. Chem. 269:7835–7838 (1994).
Endres et al., "CD4–independent infection by HIV–2 is mediated by Fusin–CXCR4," Cell 87(4):745–756 (1996).
Essani et al., "Multiple anti–cytokine activities secreted from tanapox virus–infected cells," Microbial Pathogenesis 17(5):347–353 (1994).
Graham et al., "Myxoma virus M11L ORF encodes a protein for which cell surface localization is critical in manifestation of viral virulence," Virol. 191:112–124 (1992).
Graham et al., "The T1–35kDa family of poxvirus–secreted proteins bind chemokines and modulate leukocyte influx into virus–infected tissues," Virology 229(1):12–24 (1997).
Horuk et al., "Molecular properties of the chemokine receptor family," Trends Pharm. Sci 15:159–165 (1994).
Hu et al., "Cowpox virus contains two copies of an early gene encoding a soluble secreted form of the type II TNF receptor," Virology 204(1):343–356 (1994).
Kotwal et al., "Regulation of cytokine secretion by poxvirus encoded proteins," Adv. In Exp. Med. and Biol. 351, eds. Lindley, Westeick, and Kunkel, Plenum Press, NY (1992).
Lomas et al., "Inhibition of plasmin, urokinase, tissue plasminogen activator, and $C_{1S}$ by a myxoma virus serine proteinase inhibitor," J. Biol. Chem. 268:516–521 (1993).
Macen et al., "SERP1, a serine proteinase inhibitor encoded by myxoma virus, is a secreted glycoprotein that interferes with inflammation," Virol. 195:348–363 (1993).
McFadden, "Rabbit, hare, squirrel and swine poxviruses," Encyclopedia of Virology pp. 1153–1160 (1997).
McFadden et al., "Myxoma T2 proteins as a model for poxvirus TNF receptor homologs," Journal of Neuroimmunology 72(2):119–126 (1997).
McFadden et al., Interruption of cytokine networks by poxviruses: lessons from myxoma virus, J. Leukocyte Biol. 57(5):731–738 (1995).
Mossman et al., "Myxoma virus M–T7, a secreted homolog of the interferon–gamma receptor, is a critical virulence factor for the development of myxomatosis in European rabbits," Virology 215(1):17–30 (1996).
Mossman et al., "The myxoma virus–soluble interferon–gamma receptor homolog, M–T7, inhibits interferon–gamma in a species specific manner," J. Biol. Chem. 270(7):3031–3038 (1995).
Mossman et al., "Species specificity of ectromelia virus and vaccinia virus interferon–gamma binding proteins," Virology 208(2):762–769 (1995).
Mossman et al., "Interferon–γ receptors encoded by poxviruses," Viroreceptors, Virokines And Related Immune Modulators Encoded by DNA Viruses pp. 41–54 Ed: McFadden, R.G. Landers Co. (1994).
Neote et al., "Molecular cloning, functional expression, and signaling characteristics of a C–C chemokine receptor," Cell 72:415–425 (1993).
Neurath et al., "Search for Hepatitis B virus cell receptors reveals binding sites for interleukin 7 on the virus envelope protein," J. Exp. Med. 175(2):461–470 (1992).
Opgenorth et al., "Deletion of the growth factor gene related to EGF and TGFα reduces virulence of malignant rabbit fibroma virus," Virol. 186:175–191 (1992).

(List continued on next page.)

*Primary Examiner*—Elizabeth Kemmerer
*Assistant Examiner*—Sandra Wegert
(74) *Attorney, Agent, or Firm*—Clark & Elbing LLP; Kristina Bieker-Brady

(57) ABSTRACT

The present invention provides a method of use for a novel chemokine binding protein 5(type-2 CBP) encoded by poxviruses and having amino acid sequence homology with the Shope fibroma virus T1 family of proteins against disease syndromes associated with acute or chronic dysregulated inflammatory responses.

5 Claims, 5 Drawing Sheets

OTHER PUBLICATIONS

Opgenorth et al., "Transforming growth factor alpha, shope fibroma growth factor, and vaccinia growth factor can replace myxoma growth factor in the induction of myxomatosis in rabbits," Virol. 192:701–708 (1993).

Opgenorth et al., "Deletion analysis of two tandemly arranged virulence genes in myxoma virus, M11L and myxoma growth factor," J. Virol. 66:4720–4731 (1992).

Powell et al., "An I–kappa–B homolog encoded by African swine fever virus provides a novel mechanism for down-regulation of proinflammatory cytokine responses in host macrophages," J. Virol. 70(12):8527–8533 (1996).

Schreiber et al., "The myxoma virus TNF–receptor homologue (T2) inhibits tumor necrosis factor–alpha in a species–specific fashion," Virology 204:692–705 (1994).

Sedger et al., "M–T2: A poxvirus TNF receptor homologue with dual activities," Immunology and Cell Biology 74:538–545 (1996).

Smith et al., "T2 open reading frame from the shope fibroma virus encodes a soluble form of the TNF receptor," Biochem. Biophys. Res. Commun. 176(1):335–342 (1991).

Smith, "Virus proteins that bind cytokines, chemokines or interferons," Curr. Opin. Immunol. 8:467–471 (1996).

Symons et al., "Vaccinia virus encodes a soluble type I interferon receptor of nvoel structure and broad species specificity," Cell 81:551–560 (1995).

Trkola et al., "CD4–dependent, antibody–sensitive interactions between HIV–1 and its co–receptor CCR–5," Nature 384:184–187 (1996).

Upton et al., "Tumorigenic poxviruses: genomic organization and DNA sequence of the telomeric region of the shope fibroma virus genome," Virol. 160:20–30 (1987).

Upton et al., "Encoding of a homolog of the IFN–gamma receptor by myxoma virus," Science 258:1369–1372 (1992).

Upton et al., "Mapping and sequence of a gene from myxoma virus that is related to those encoding epidermal growth factor and transforming growth factor alpha," J. Virol. 61(4):1271–1275 (1987).

Upton et al., "Myxoma virus and malignant rabbit fibroma virus encode a serpin–like protein important for virus virulence," Virol. 179:618–631 (1990).

Upton et al., "Myxoma virus expresses a secreted protein with homology to the tumor necrosis factor receptor gene family that contributes to viral virulence," Virology 184:370–382 (1991).

Upton et al., "Detection of viral homologs of cellular interferon gamma receptors," Methods in Molecular Genetics 4:383–390 (1994).

Wu e tal., "CD4–induced interaction of primary HIV–1 gp120 glycoproteins with the chemokine receptor CCR–5," Nature 384:179–183 (1996).

Callard, et al. 1994 The Cytokine Facts Book. Academic Press, pp. 75–76, 146–147, 181–183, 184–187, 223–224, 226–227.*

Bork, P. (1996), Go hunting in sequence databases but watch out for the traps. Trends Genetics, 12(10):425–427.*

Bork, P. (1998), Powers and Pitfalls in Sequence Analysis: The 70% Hurdle, Genome Res., 10:398–400, esp. p. 400.*

Doerks, T. (1998), Protein annotation: detective work for function prediction., Trends Genetics. 14(6):248–250.*

Skolnick, J. (200), From genes to protein structure and function: novel applications of computational approaches in the genomic era., trends Biotech., 18(1):34–39, esp. p. 36.*

Brenner, S. (1999) Errors in genome annotation, Trends in Genetics, 15(4): 3–4, esp. Fig. 2.*

Smith, T.F. and Zhang, X. (1997) The challenges of genome sequence annotation or "The devil is in the details", Nature Biotechnology, 15: 1222–1223.*

* cited by examiner

```
                              1                                                   50
(SEQ ID NO: 8)    RPV35kd                     MPAS LQQSS
(SEQ ID NO: 7) VVlis35kd   MKQYIVLACM CLAAAAMPAS LQQSSSSSSS CTEEENKHHM GIDVIIKVTK
(SEQ ID NO: 6) VVcop35kd   ...............MHVPAS LQQSSSSSSS CTEEENKHHM GIDVIIKVTK
(SEQ ID NO: 5)    VAR35kd  MKQYIVLACM CLAAAAMPAS LQQSS...SS CTEEENKHYM GIDVIIKVTK
(SEQ ID NO: 4)    CPV35k    MKQIVLACI CLAAVAIPTS LQQSFSSSSS CTEEENKHHM GIDVIIKVTK
(SEQ ID NO: 3)     SFV.T1   .........M RRLCIILLVY VYATFATKGI CKQDEDVRYM GIDVVVKVTK
(SEQ ID NO: 2)     MYX-T1   .........M KRLC VLFAC LAATLATKGI CRQGEDVRYM GIDAVAKITK 51                                                  100
             VVlis35kd   QDQTPTNDKI CQSVTEITES ESDPDPEVE. .......... .......SED
             VVcop35kd   QDQTPTNDKI CQSVTEITES ESDPDPEVE. .......... .......SED
               VAR35kd   QDQTPTNDKI CQSVTEITES ES..DPEVE. .......... .......SED
                CPV35k   QDQTPTNDKI CQSVTEVTES EDESEEVVK. .......... ........GD
                SFV.T1   ..KTSGSDTV CQALRTTFEA AHKGDGAND. .SLSTEYVDD YSEEEEY EY
                MYX-T1   ..RTTGSDTP CQGLRTTIES AYTEDENEDD GATGTEQPDD LSEEYEYDEN 101                                                 150
             VVlis35kd   DSTSVEDVDP PTTYYSIIGG GLRMNFGFTK CPQIKSISES ADGNTVNARL
             VVcop35kd   DSTSVEDVDP PTTYYSIIGG GLRMNFGFTK CPQIKSISES ADGNTVNARL
               VAR35kd   DSTSVEDVDP PTTYYSIIGG GLRMNFGFTK CPQIKSISES ANGNAVNARL
                CPV35k   .......... PTTYYTVVGG GLTMDFGFTK CPKISSISEY SDGNTVNARL
                SFV.T1   DESFLEGFVI GSTYYTIVGG GLSVTFGFTG CPTVKSVSEY AKGRIVFIRL
                MYX-T1   DESFLTGFVI GSTYHTIVGG GLSVTFGFTG CPTVKAISEH VKGRHVYVRL 151                                                 200
             VVlis35kd   SSVSPGQGKD SPAITREEAL AMIKDCEVSI DIRCSEEEKD SDIKTHPVLG
             VVcop35kd   SSVSPGQGKD SPAITREEAL AMIKDCEVSI DIRCSEEEKD SDIKTHPVLG
               VAR35kd   SSVPPGQGKD SPAITRAEAL AMIKDCELSI DIRCSEEEKD SDIQTHPVLG
                CPV35k   SSVSPGQGKD SPAITREEAL SMIKDCEMSI NIKCSEEEKD SNIKTHPVLG
                SFV.T1   SSDAPWRDTN PMSINRTEAL ALLEKCETSI DIKCSNETVS ETTYGLASLA
                MYX-T1   SSDAPWRDTN PVSMNRTEAL ALLDTCEVSV DIKCSRVNVT ETTYGTAALV 201                                                 250
             VVlis35kd   SNISHKKVSY EDIIGSTIVD TKCVKNLEFS VRIGDMCKES SELEVKDGFK
             VVcop35kd   SNISHKKVSY EDIIGSTIVD TKCVKNLEFS VRIGDMCKES SELEVKDGFK
               VAR35kd   SNISHKKVSY EDIIGSTIVD TKCVKNLEFS VRIGDMCKES SDLEVKDGFK
                CPV35k   SNISHKKVSY EDIIGSTIVD TKCVKNLEIS VRIGDMCKES SELEVKDGFK
                SFV.T1   PHITQATER. GNIIGSTLVD TDCVENLDVT VHLGEMCRKT SDLSKRDSLK
                MYX-T1   PRITQATRR. SHIIGSTLVD TECVKSLDIT VQVGEMCKRT SDLSARDSLK 251          276
             VVlis35kd   YVDGSASEGA TDDTSLIDST KLKACV
             VVcop35kd   YVDGSASEGA TDDTSLIDST KLKACV
               VAR35kd   YVDGSVSEGV TDDTSLIDST KLKSCV
                CPV35k   YVDGSASEDA ADDTSLINSA KLIACV
                SFV.T1   VKNGELLD.. .DDTFSIHTP KLKACN
                MYX-T1   VKNGKLLE.. .DDILVLRTP TLKACN
```

FIG. 1

(SEQ ID NO: 1) 1    TACAGCGACAGTAATCATCCCGAGGAGGTCGACGACTTCGTGGAATACCATTGGGGTACA

61   CGCCTCCGTCTCTTTCCCTCACCCAAACGATGTAGACTCGTTTCA[TAG]ATTACGGATTTT

121  CTTCTAGTTAAATTCTTAAAAAAAGTCGAATTATAATAAAACGTGGGCGTATAGAAGAA

181  CTCTATCATGAAACGCCTGTGTGTATTATTCGCGTGCCTGGCCGCGACCCTCGCGACGAA
(SEQ ID NO: 2)      M   K   R   L   C   V   L   F   A   C   L   A   A   T   L   A ↑ T   K

241  GGGCATCTGCAGACAAGGCGAAGATGTCCGATACATGGGAATAGACGTCGTGGCCAAAAT
      G   I   C   R   Q   G   E   D   V   R   Y   M   G   I   D   V   V   A   K   I

301  TACAAAGAGGACTACCGGAAGCGACACGCCGTGTCAGGGTCTGCGTACGACTATTGAATC
      T   K   R   T   T   G   S   D   T   P   C   Q   G   L   R   T   T   I   E   S

361  CGCGTATACAGAAGACGAAAACGAAGACGATGGCGCGACGGGTACGGAGCAGCCCGACGA
      A   Y   T   E   D   E   N   E   D   D   G   A   T   G   T   E   Q   P   D   D

421  TCTTAGCGAGGAATACGAGTACGACGAAAACGACGAATCGTTTCTAACCGGTTTCGTGAT
      L   S   E   E   Y   E   Y   D   E   N   D   E   S   F   L   T   G   F   V   I

481  CGGAAGTACTTACCACACGATCGTCGGAGGAGGACTCTCCGTCACGTTCGGATTTACGGG
      G   S   T   Y   H   T   I   V   G   G   G   L   S   V   T   F   G   F   T   G

541  ATGTCCTACCGTTAAGGCGATATCCGAACACGTCAAAGGACGCCACGTCTACGTCCGACT
      C   P   T   V   K   A   I   S   E   H   V   K   G   R   H   V   Y   V   R   L

601  GTCCAGCGACGCTCCTTGGAGAGATACGAATCCCGTGTCTATGAACCGTACAGAGGCGCT
      S   S   D   A   P   W   R   D   T   N   P   V   S   M   N   R   T   E   A   L

661  CGCCCTACTCGACACGTGTGAAGTGTCCGTAGATATCAAATGCAGTCGCGTCAACGTAAC
      A   L   L   D   T   C   E   V   S   V   D   I   K   C   S   R   V   N   V   T

721  CGAAACGACGTACGGAACCGCGGCGCTTGTCCCGCGTATAACTCAAGCGACGAGACGCAG
      E   T   T   Y   G   T   A   A   L   V   P   R   I   T   Q   A   T   R   R   S

781  TCATATTATCGGATCTACCCTGGTCGACACGGAATGTGTGAAGAGTCTAGACATAACCGT
      H   I   I   G   S   T   L   V   D   T   E   C   V   K   S   L   D   I   T   V

841  CCAAGTGGGTGAAATGTGTAAGAGAACGTCTGATCTCTCGGCGAGAGACAGTCTTAAGGT
      Q   V   G   E   M   C   K   R   T   S   D   L   S   A   R   D   S   L   K   V

901  AAAGAACGGCAAACTACTCGAGGACGATATCCTTGTCCTTCGTACGCCTACCCTCAAGGC
      K   N   G   K   L   L   E   D   D   I   L   V   L   R   T   P   T   L   K   A

961  GTGTAACTAATCCTATCTACGATCGATGTCGTATTTTTCTGACCGTTACGCGTCACGTTT
      C   N

1021 TTATACCTATATAAAYAGKTAAAACCCATATAGGGAATACCGCTCGCTTTTTTTTCCTTC

1081 GTAGTTGTTTACCCGCTCGATAGATCGCGTCGAGGAAGTACCAACCGTGACCACTCCTCC

1141 GGCGGGGATCC

FIG. 2

```
(SEQ ID NO:9)    1    TACAGCGACAGTAATCATCCCGAGGAGGTCGACGACTTCGTGGAATACCATTGGGGTACA

61    CGCCTCCGTCTCTTTCCCTCACCCAAACGATGTAGACTCGTTTCATAGATTACGGATTTT

121    CTTCTAGTTAAATTCTTAAAAAAAAGTCGAATTATAATAAAACGTGGGCGTATAGAAGAA

181    CTCTATCATGAAACGCCTGTGTGTATTATTCGCGTGCCTGGCCGCGACCCTCGCGACGAA
(SEQ ID NO:10)          M   K   R   L   C   V   L   F   A   C   L   A   A   T   L   A   T   K

241    GGGCATCTGCAGACAAGGCGAAGATGTCCGATACATGGGAATAGACGTCGTGGCCAAAAT
                       G   I   C   R   Q   G   E   D   V   R   Y   M   G   I   D   V   V   A   K   I

301    TACAAAGAGGACTACCGGAAGCGACACGCCGTGTCAGGGTCTGCGTACGACTATTGAATC
                       T   K   R   T   T   G   S   D   T   P   C   Q   G   L   R   T   T   I   E   S

361    CGCGTATACAGAAGACGAAAACGAAGACGATGGCGCGACGGGTACGGAGCAGCCCGACGA
                       A   Y   T   E   D   E   N   E   D   D   G   A   T   G   T   E   Q   P   D   D

421    TCTTAGCGAGGAATACGAGTACGACGAAAACGACGAATCGTTTCTAACCGGTTTCGTGAT
                       L   S   E   E   Y   E   Y   D   E   N   D   E   S   F   L   T   G   F   V   I

481    CGGAAGTACTTACCACACGATCGTCGGAGGAGGACTCTCCGTCACGTTCGGATTTACGGG
                       G   S   T   Y   H   T   I   V   G   G   G   L   S   V   T   F   G   F   T   G

541    ATGTCCTACCGTTAAGGCGATATCCGAACACGTCAAAGGACGCCACGTCTACGTCCGACT
                       C   P   T   V   K   A   I   S   E   H   V   K   G   R   H   V   Y   V   R   L

601    GTCCAGCGACGCTCCTTGGAGAGATACGAATCCCGTGTCTATGAACCGTACAGAGGCGCT
                       S   S   D   A   P   W   R   D   T   N   P   V   S   M   N   R   T   E   A   L

661    CGCCCTACTCGACACGTGTGAAGTGTCCGTAGATATCAAATGCAGTCGCGTCAACGTAAC
                       A   L   L   D   T   C   E   V   S   V   D   I   K   C   S   R   V   N   V   T

721    CGAAACGACGTACGGAACCGCGGCGCTTGTCCCGCGTATAACTCAAGCGACGAGACGCAG
                       E   T   T   Y   G   T   A   A   L   V   P   R   I   T   Q   A   T   R   R   S

781    TCATATTATCGGATCTACCCTGGTCGACACGGAATGTGTGAAGAGTCTAGACATAACCGT
                       H   I   I   G   S   T   L   V   D   T   E   C   V   K   S   L   D   I   T   V

841    CCAAGTGGGTGAAATGTGTAAGAGAACGTCTGATCTCTCGGCGAGAGACAGTCTTAAGGT
                       Q   V   G   E   M   C   K   R   T   S   D   L   S   A   R   D   S   L   K   V

901    AAAGAACGGCAAACTACTCGAGGACGATATCCTTGTCCTTCGTACGCCTACCCTCAAGGC
                       K   N   G   K   L   L   E   D   D   I   L   V   L   R   T   P   T   L   K   A

961    GTGTAACTAATCCTATCTACGATCGATGTCGTATTTTTCTGACCGTTACGCGTCACGTTT
                       C   N

1021    TTATACCTATATAAAYAGKTAAAACCCATATAGGGAATACCGCTCGCTTTTTTTTCCTTC

1081    GTAGTTGTTTACCCGCTCGATAGATCGCGTCGAGGAAGTACCAACCGTGACCACTCCTCC

1141    GGCGGGGATCC
```

FIG. 5

SEQUENCE LISTING

<160> NUMBER OF SEQ ID NOS: 10

<210> SEQ ID NO 1
<211> LENGTH: 1151
<212> TYPE: DNA
<213> ORGANISM: Myxoma virus

<400> SEQUENCE: 1

```
tacagcgaca gtaatcatcc cgaggaggtc gacgacttcg tggaatacca ttggggtaca      60
cgcctccgtc tctttccctc acccaaacga tgtagactcg tttcatagat tacggatttt     120
cttctagtta aattcttaaa aaaagtcga attataataa aacgtgggcg tatagaagaa     180
ctctatcatg aaacgcctgt gtgtattatt cgcgtgcctg gccgcgaccc tcgcgacgaa     240
gggcatctgc agacaaggcg aagatgtccg atacatggga atagacgccg tggccaaaat     300
tacaaagagg actaccggaa gcgacacgcc gtgtcagggt ctgcgtacga ctattgaatc     360
cgcgtataca gaagacgaaa acgaagacga tggcgcgacg ggtacggagc agcccgacga     420
tcttagcgag gaatacgagt acgacgaaaa cgacgaatcg tttctaaccg gtttcgtgat     480
cggaagtact taccacacga tcgtcggagg aggactctcc gtcacgttcg gatttacggg     540
atgtcctacc gttaaggcga tatccgaaca cgtcaaagga cgccacgtct acgtccgact     600
gtccagcgac gctccttgga gagatacgaa tcccgtgtct atgaaccgta cagaggcgct     660
cgccctactc gacacgtgtg aagtgtccgt agatatcaaa tgcagtcgcg tcaacgtaac     720
cgaaacgacg tacggaaccg cggcgcttgt cccgcgtata actcaagcga cgagacgcag     780
```

```
tcatattatc ggatctaccc tggtcgacac ggaatgtgtg aagagtctag acataaccgt    840
ccaagtgggt gaaatgtgta agagaacgtc tgatctctcg gcgagagaca gtcttaaggt    900
aaagaacggc aaactactcg aggacgatat ccttgtcctt cgtacgccta ccctcaaggc    960
gtgtaactaa tcctatctac gatcgatgtc gtattttcct gaccgttacg cgtcacgttt   1020
ttatacctat ataaaygkt aaaacccata tagggaatac cgctcgcttt tttttccttc    1080
gtagttgttt acccgctcga tagatcgcgt cgaggaagta ccaaccgtga ccactcctcc   1140
ggcggggatc c                                                        1151
```

<210> SEQ ID NO 2
<211> LENGTH: 260
<212> TYPE: PRT
<213> ORGANISM: Myxoma virus

<400> SEQUENCE: 2

```
Met Lys Arg Leu Cys Val Leu Phe Ala Cys Leu Ala Ala Thr Leu Ala
 1               5                  10                  15

Thr Lys Gly Ile Cys Arg Gln Gly Glu Asp Val Arg Tyr Met Gly Ile
            20                  25                  30

Asp Ala Val Ala Lys Ile Thr Lys Arg Thr Thr Gly Ser Asp Thr Pro
        35                  40                  45

Cys Gln Gly Leu Arg Thr Thr Ile Glu Ser Ala Tyr Thr Glu Asp Glu
    50                  55                  60

Asn Glu Asp Asp Gly Ala Thr Gly Thr Glu Gln Pro Asp Asp Leu Ser
65                  70                  75                  80

Glu Glu Tyr Glu Tyr Asp Glu Asn Asp Glu Ser Phe Leu Thr Gly Phe
                85                  90                  95

Val Ile Gly Ser Thr Tyr His Thr Ile Val Gly Gly Gly Leu Ser Val
            100                 105                 110

Thr Phe Gly Phe Thr Gly Cys Pro Thr Val Lys Ala Ile Ser Glu His
        115                 120                 125

Val Lys Gly Arg His Val Tyr Val Arg Leu Ser Ser Asp Ala Pro Trp
    130                 135                 140

Arg Asp Thr Asn Pro Val Ser Met Asn Arg Thr Glu Ala Leu Ala Leu
145                 150                 155                 160

Leu Asp Thr Cys Glu Val Ser Val Asp Ile Lys Cys Ser Arg Val Asn
                165                 170                 175

Val Thr Glu Thr Thr Tyr Gly Thr Ala Ala Leu Val Pro Arg Ile Thr
            180                 185                 190

Gln Ala Thr Arg Arg Ser His Ile Ile Gly Ser Thr Leu Val Asp Thr
        195                 200                 205

Glu Cys Val Lys Ser Leu Asp Ile Thr Val Gln Val Gly Glu Met Cys
    210                 215                 220

Lys Arg Thr Ser Asp Leu Ser Ala Arg Asp Ser Leu Lys Val Lys Asn
225                 230                 235                 240

Gly Lys Leu Leu Glu Asp Asp Ile Leu Val Leu Arg Thr Pro Thr Leu
                245                 250                 255

Lys Ala Cys Asn
            260
```

<210> SEQ ID NO 3
<211> LENGTH: 258
<212> TYPE: PRT
<213> ORGANISM: Shope fibroma virus -continued

<400> SEQUENCE: 3

```
Met Arg Arg Leu Cys Ile Ile Leu Leu Val Tyr Val Tyr Ala Thr Phe
 1               5                  10                  15

Ala Thr Lys Gly Ile Cys Lys Gln Asp Glu Asp Val Arg Tyr Met Gly
            20                  25                  30

Ile Asp Val Val Val Lys Val Thr Lys Lys Thr Ser Gly Ser Asp Thr
        35                  40                  45

Val Cys Gln Ala Leu Arg Thr Thr Phe Glu Ala Ala His Lys Gly Asp
    50                  55                  60

Gly Ala Asn Asp Ser Leu Ser Thr Glu Tyr Val Asp Asp Tyr Ser Glu
65                  70                  75                  80

Glu Glu Glu Tyr Glu Tyr Asp Glu Ser Phe Leu Glu Gly Phe Val Ile
                85                  90                  95

Gly Ser Thr Tyr Tyr Thr Ile Val Gly Gly Gly Leu Ser Val Thr Phe
            100                 105                 110

Gly Phe Thr Gly Cys Pro Thr Val Lys Ser Val Ser Glu Tyr Ala Lys
        115                 120                 125

Gly Arg Ile Val Phe Ile Arg Leu Ser Ser Asp Ala Pro Trp Arg Asp
    130                 135                 140

Thr Asn Pro Met Ser Ile Asn Arg Thr Glu Ala Leu Ala Leu Leu Glu
145                 150                 155                 160

Lys Cys Glu Thr Ser Ile Asp Ile Lys Cys Ser Asn Glu Thr Val Ser
                165                 170                 175

Glu Thr Thr Tyr Gly Leu Ala Ser Leu Ala Pro His Ile Thr Gln Ala
            180                 185                 190

Thr Glu Arg Gly Asn Ile Ile Gly Ser Thr Leu Val Asp Thr Asp Cys
        195                 200                 205

Val Glu Asn Leu Asp Val Thr Val His Leu Gly Glu Met Cys Arg Lys
    210                 215                 220

Thr Ser Asp Leu Ser Lys Arg Asp Ser Leu Lys Val Lys Asn Gly Glu
225                 230                 235                 240

Leu Leu Asp Asp Asp Thr Phe Ser Ile His Thr Pro Lys Leu Lys Ala
                245                 250                 255

Cys Asn
```

<210> SEQ ID NO 4
<211> LENGTH: 246
<212> TYPE: PRT
<213> ORGANISM: Cowpox virus

<400> SEQUENCE: 4

```
Met Lys Gln Ile Val Leu Ala Cys Ile Cys Leu Ala Ala Val Ala Ile
 1               5                  10                  15

Pro Thr Ser Leu Gln Gln Ser Phe Ser Ser Ser Ser Ser Cys Thr Glu
            20                  25                  30

Glu Glu Asn Lys His His Met Gly Ile Asp Val Ile Ile Lys Val Thr
        35                  40                  45

Lys Gln Asp Gln Thr Pro Thr Asn Asp Lys Ile Cys Gln Ser Val Thr
    50                  55                  60

Glu Val Thr Glu Ser Glu Asp Glu Ser Glu Glu Val Val Lys Gly Asp
65                  70                  75                  80

Pro Thr Thr Tyr Tyr Thr Val Val Gly Gly Gly Leu Thr Met Asp Phe
                85                  90                  95

Gly Phe Thr Lys Cys Pro Lys Ile Ser Ser Ile Ser Glu Tyr Ser Asp
```

```
              100                 105                 110
Gly Asn Thr Val Asn Ala Arg Leu Ser Ser Val Ser Pro Gly Gln Gly
            115                 120                 125

Lys Asp Ser Pro Ala Ile Thr Arg Glu Glu Ala Leu Ser Met Ile Lys
130                 135                 140

Asp Cys Glu Met Ser Ile Asn Ile Lys Cys Ser Glu Glu Lys Asp
145                 150                 155                 160

Ser Asn Ile Lys Thr His Pro Val Leu Gly Ser Asn Ile Ser His Lys
            165                 170                 175

Lys Val Ser Tyr Glu Asp Ile Ile Gly Ser Thr Ile Val Asp Thr Lys
            180                 185                 190

Cys Val Lys Asn Leu Glu Ile Ser Val Arg Ile Gly Asp Met Cys Lys
            195                 200                 205

Glu Ser Ser Glu Leu Glu Val Lys Asp Gly Phe Lys Tyr Val Asp Gly
            210                 215                 220

Ser Ala Ser Glu Asp Ala Ala Asp Asp Thr Ser Leu Ile Asn Ser Ala
225                 230                 235                 240

Lys Leu Ile Ala Cys Val
                245

<210> SEQ ID NO 5
<211> LENGTH: 253
<212> TYPE: PRT
<213> ORGANISM: Variola virus

<400> SEQUENCE: 5

Met Lys Gln Tyr Ile Val Leu Ala Cys Met Cys Leu Ala Ala Ala Ala
1               5                  10                  15

Met Pro Ala Ser Leu Gln Gln Ser Ser Ser Cys Thr Glu Glu Glu
            20                  25                  30

Asn Lys His Tyr Met Gly Ile Asp Val Ile Ile Lys Val Thr Lys Gln
            35                  40                  45

Asp Gln Thr Pro Thr Asn Asp Lys Ile Cys Gln Ser Val Thr Glu Ile
    50                  55                  60

Thr Glu Ser Glu Ser Asp Pro Glu Val Glu Ser Glu Asp Asp Ser Thr
65                  70                  75                  80

Ser Val Glu Asp Val Asp Pro Thr Thr Tyr Tyr Ser Ile Ile Gly
                85                  90                  95

Gly Gly Leu Arg Met Asn Phe Gly Phe Thr Lys Cys Pro Gln Ile Lys
                100                 105                 110

Ser Ile Ser Glu Ser Ala Asn Gly Asn Ala Val Asn Ala Arg Leu Ser
            115                 120                 125

Ser Val Pro Pro Gly Gln Gly Lys Asp Ser Pro Ala Ile Thr Arg Ala
            130                 135                 140

Glu Ala Leu Ala Met Ile Lys Asp Cys Glu Leu Ser Ile Asp Ile Arg
145                 150                 155                 160

Cys Ser Glu Glu Lys Asp Ser Asp Ile Gln Thr His Pro Val Leu
            165                 170                 175

Gly Ser Asn Ile Ser His Lys Lys Val Ser Tyr Glu Asp Ile Ile Gly
                180                 185                 190

Ser Thr Ile Val Asp Thr Lys Cys Val Lys Asn Leu Glu Phe Ser Val
            195                 200                 205

Arg Ile Gly Asp Met Cys Lys Glu Ser Ser Asp Leu Glu Val Lys Asp
    210                 215                 220
```

-continued

Gly Phe Lys Tyr Val Asp Gly Ser Val Ser Glu Gly Val Thr Asp Asp
225 230 235 240

Thr Ser Leu Ile Asp Ser Thr Lys Leu Lys Ser Cys Val
245 250

<210> SEQ ID NO 6
<211> LENGTH: 244
<212> TYPE: PRT
<213> ORGANISM: Vaccinia virus Copenhagen

<400> SEQUENCE: 6

Met His Val Pro Ala Ser Leu Gln Gln Ser Ser Ser Ser Ser Ser Ser
1 5 10 15

Cys Thr Glu Glu Glu Asn Lys His His Met Gly Ile Asp Val Ile Ile
20 25 30

Lys Val Thr Lys Gln Asp Gln Thr Pro Thr Asn Asp Lys Ile Cys Gln
35 40 45

Ser Val Thr Glu Ile Thr Glu Ser Glu Ser Asp Pro Asp Pro Glu Val
50 55 60

Glu Ser Glu Asp Asp Ser Thr Ser Val Glu Asp Val Asp Pro Pro Thr
65 70 75 80

Thr Tyr Tyr Ser Ile Ile Gly Gly Gly Leu Arg Met Asn Phe Gly Phe
85 90 95

Thr Lys Cys Pro Gln Ile Lys Ser Ile Ser Glu Ser Ala Asp Gly Asn
100 105 110

Thr Val Asn Ala Arg Leu Ser Ser Val Ser Pro Gly Gln Gly Lys Asp
115 120 125

Ser Pro Ala Ile Thr Arg Glu Glu Ala Leu Ala Met Ile Lys Asp Cys
130 135 140

Glu Val Ser Ile Asp Ile Arg Cys Ser Glu Glu Glu Lys Asp Ser Asp
145 150 155 160

Ile Lys Thr His Pro Val Leu Gly Ser Asn Ile Ser His Lys Lys Val
165 170 175

Ser Tyr Glu Asp Ile Ile Gly Ser Thr Ile Val Asp Thr Lys Cys Val
180 185 190

Lys Asn Leu Glu Phe Ser Val Arg Ile Gly Asp Met Cys Lys Glu Ser
195 200 205

Ser Glu Leu Glu Val Lys Asp Gly Phe Lys Tyr Val Asp Gly Ser Ala
210 215 220

Ser Glu Gly Ala Thr Asp Asp Thr Ser Leu Ile Asp Ser Thr Lys Leu
225 230 235 240

Lys Ala Cys Val

<210> SEQ ID NO 7
<211> LENGTH: 258
<212> TYPE: PRT
<213> ORGANISM: Vaccinia virus Lister

<400> SEQUENCE: 7

Met Lys Gln Tyr Ile Val Leu Ala Cys Met Cys Leu Ala Ala Ala Ala
1 5 10 15

Met Pro Ala Ser Leu Gln Gln Ser Ser Ser Ser Ser Ser Ser Cys Thr
20 25 30

Glu Glu Glu Asn Lys His His Met Gly Ile Asp Val Ile Ile Lys Val
35 40 45

Thr Lys Gln Asp Gln Thr Pro Thr Asn Asp Lys Ile Cys Gln Ser Val

-continued

```
    50                  55                  60

Thr Glu Ile Thr Glu Ser Glu Ser Asp Pro Asp Pro Glu Val Glu Ser
65                  70                  75                  80

Glu Asp Asp Ser Thr Ser Val Glu Asp Val Asp Pro Pro Thr Thr Tyr
                85                  90                  95

Tyr Ser Ile Ile Gly Gly Gly Leu Arg Met Asn Phe Gly Phe Thr Lys
            100                 105                 110

Cys Pro Gln Ile Lys Ser Ile Ser Glu Ser Ala Asp Gly Asn Thr Val
        115                 120                 125

Asn Ala Arg Leu Ser Ser Val Ser Pro Gly Gln Gly Lys Asp Ser Pro
    130                 135                 140

Ala Ile Thr Arg Glu Glu Ala Leu Ala Met Ile Lys Asp Cys Glu Val
145                 150                 155                 160

Ser Ile Asp Ile Arg Cys Ser Glu Glu Glu Lys Asp Ser Asp Ile Lys
                165                 170                 175

Thr His Pro Val Leu Gly Ser Asn Ile Ser His Lys Lys Val Ser Tyr
            180                 185                 190

Glu Asp Ile Ile Gly Ser Thr Ile Val Asp Thr Lys Cys Val Lys Asn
        195                 200                 205

Leu Glu Phe Ser Val Arg Ile Gly Asp Met Cys Lys Glu Ser Ser Glu
    210                 215                 220

Leu Glu Val Lys Asp Gly Phe Lys Tyr Val Asp Gly Ser Ala Ser Glu
225                 230                 235                 240

Gly Ala Thr Asp Asp Thr Ser Leu Ile Asp Ser Thr Lys Leu Lys Ala
                245                 250                 255

Cys Val

<210> SEQ ID NO 8
<211> LENGTH: 9
<212> TYPE: PRT
<213> ORGANISM: Rabbit poxvirus

<400> SEQUENCE: 8

Met Pro Ala Ser Leu Gln Gln Ser Ser
 1               5

<210> SEQ ID NO 9
<211> LENGTH: 1151
<212> TYPE: DNA
<213> ORGANISM: Myxoma virus

<400> SEQUENCE: 9
tacagcgaca gtaatcatcc cgaggaggtc gacgacttcg tggaatacca ttggggtaca      60
cgcctccgtc tctttccctc acccaaacga tgtagactcg tttcatagat tacggatttt     120
cttctagtta aattcttaaa aaaaagtcga attataataa aacgtgggcg tatagaagaa     180
ctctatcatg aaacgcctgt gtgtattatt cgcgtgcctg gccgcgaccc tcgcgacgaa     240
gggcatctgc agacaaggcg aagatgtccg atacatggga atagacgtcg tggccaaaat     300
tacaaagagg actaccggaa gcgacacgcc gtgtcagggt ctgcgtacga ctattgaatc     360
cgcgtataca gaagacgaaa acgaagacga tggcgcgacg ggtacggagc agcccgacga     420
tcttagcgag gaatacgagt acgacgaaaa cgacgaatcg tttctaaccg gtttcgtgat     480
cggaagtact taccacacga tcgtcggagg aggactctcc gtcacgttcg gatttacggg     540
atgtcctacc gttaaggcga tatccgaaca cgtcaaagga cgccacgtct acgtccgact     600
```

-continued

| | |
|---|---|
| gtccagcgac gctccttgga gagatacgaa tcccgtgtct atgaaccgta cagaggcgct | 660 |
| cgccctactc gacacgtgtg aagtgtccgt agatatcaaa tgcagtcgcg tcaacgtaac | 720 |
| cgaaacgacg tacggaaccg cggcgcttgt cccgcgtata actcaagcga cgagacgcag | 780 |
| tcatattatc ggatctaccc tggtcgacac ggaatgtgtg aagagtctag acataaccgt | 840 |
| ccaagtgggt gaaatgtgta agagaacgtc tgatctctcg gcgagagaca gtcttaaggt | 900 |
| aaagaacggc aaactactcg aggacgatat ccttgtcctt cgtacgccta ccctcaaggc | 960 |
| gtgtaactaa tcctatctac gatcgatgtc gtattttct gaccgttacg cgtcacgttt | 1020 |
| ttatacctat ataaayagkt aaaacccata tagggaatac cgctcgcttt ttttccttc | 1080 |
| gtagttgttt acccgctcga tagatcgcgt cgaggaagta ccaaccgtga ccactcctcc | 1140 |
| ggcggggatc c | 1151 |

<210> SEQ ID NO 10
<211> LENGTH: 260
<212> TYPE: PRT
<213> ORGANISM: Myxoma virus

<400> SEQUENCE: 10

Met Lys Arg Leu Cys Val Leu Phe Ala Cys Leu Ala Ala Thr Leu Ala
1               5                   10                  15

Thr Lys Gly Ile Cys Arg Gln Gly Glu Asp Val Arg Tyr Met Gly Ile
            20                  25                  30

Asp Val Val Ala Lys Ile Thr Lys Arg Thr Thr Gly Ser Asp Thr Pro
        35                  40                  45

Cys Gln Gly Leu Arg Thr Thr Ile Glu Ser Ala Tyr Thr Glu Asp Glu
    50                  55                  60

Asn Glu Asp Asp Gly Ala Thr Gly Thr Glu Gln Pro Asp Asp Leu Ser
65                  70                  75                  80

Glu Glu Tyr Glu Tyr Asp Glu Asn Asp Glu Ser Phe Leu Thr Gly Phe
                85                  90                  95

Val Ile Gly Ser Thr Tyr His Thr Ile Val Gly Gly Gly Leu Ser Val
            100                 105                 110

Thr Phe Gly Phe Thr Gly Cys Pro Thr Val Lys Ala Ile Ser Glu His
        115                 120                 125

Val Lys Gly Arg His Val Tyr Val Arg Leu Ser Ser Asp Ala Pro Trp
    130                 135                 140

Arg Asp Thr Asn Pro Val Ser Met Asn Arg Thr Glu Ala Leu Ala Leu
145                 150                 155                 160

Leu Asp Thr Cys Glu Val Ser Val Asp Ile Lys Cys Ser Arg Val Asn
                165                 170                 175

Val Thr Glu Thr Thr Tyr Gly Thr Ala Ala Leu Val Pro Arg Ile Thr
            180                 185                 190

Gln Ala Thr Arg Arg Ser His Ile Ile Gly Ser Thr Leu Val Asp Thr
        195                 200                 205

Glu Cys Val Lys Ser Leu Asp Ile Thr Val Gln Val Gly Glu Met Cys
    210                 215                 220

Lys Arg Thr Ser Asp Leu Ser Ala Arg Asp Ser Leu Lys Val Lys Asn
225                 230                 235                 240

Gly Lys Leu Leu Glu Asp Asp Ile Leu Val Leu Arg Thr Pro Thr Leu
                245                 250                 255

Lys Ala Cys Asn
            260

MYXOMA CHEMOKINE BINDING PROTEIN

This application is a CIP of and claims priority from U.S. patent application Ser. No. 09/180,877, filed on Apr. 2, 1999 now abandoned.

BACKGROUND OF THE INVENTION

1. Field of the Invention

This invention relates generally to the field of immunology and specifically to a chemokine binding protein encoded by a variety of poxviruses and methods of use therefor.

2. Description of Related Art

It is becoming increasingly clear that viruses which make their living within cells of higher-order vertebrates must have evolved to specifically avoid the host immune system (Gooding, L., Cell, 91:5–7, 1992; Marrack, P. and Kappler, J., Cell, 76:323–332, 1994; Smith, G., Trends in Micro., 82:80–88, 1994). In fact, virus survival is dependent upon strategies which can evade, suppress, counteract, or otherwise confound the myriad of host responses to a foreign invader. The selection pressure conferred by the effector arms of the immune system can clearly be a powerful element of evolutionary pressure, and all eukaryotic viruses existing today contain imprints or remnants of their battles with the immune system, either as encoded proteins or as evidenced by their particular biological survival strategies.

The larger DNA viruses (i.e. the adenoviruses, herpesviruses, iridoviruses and poxviruses) specifically encode proteins that function to protect the virus from immune recognition and/or clearance by the infected host. Such "subversive" viral proteins are now providing information concerning the functional operations of the immune system, and it is likely that many more discoveries of new members of this growing family will be identified in the future.

In the 1980's the term "virokine" was proposed to describe virus-encoded proteins secreted from infected cells which function by mimicking extracellular signaling molecules such as cytokines or other secreted regulators important for the host immune repertoire (Kotwal, G. and Moss, B., Nature, 335:176–178, 1988). Later, in the 1990's the term "viroceptor" was introduced to account for the observation that some virus encoded proteins that mimic important cellular receptors and function by diverting host cytokines away from their normal receptors, thus interrupting the immune circuitry at its earliest stages (Upton, et al., Virology, 184:370, 1991; Schreiber and McFadden, Virology, 204:692–705, 1994).

Recent studies on a particular poxvirus, myxoma virus, have shown that the virus disrupts the immune system by a variety of strategies (McFadden and Graham, Seminars in Virology, 5:421–429, 1994). Myxoma virus is the infectious agent of a virulent systemic disease of domestic rabbits called myxomatosis. Originally described in the last century, myxoma was the first virus pathogen discovered for a laboratory animal and was the first viral agent ever deliberately introduced into the environment for the explicit purpose of pest eradication. Since its release into the Australian and European feral rabbit populations more than 40 years ago, the field strains of both the rabbit and virus have been subjected to mutual evolutionary and selective pressures that have resulted in a steady-state enzootic in the inoculated areas (Fenner, F. and Ratcliffe, F. N., "Myxomatosis", Cambridge University Press, London, 1965).

Myxoma shares many of the biologic features associated with other poxviruses, namely cytoplasmic location of replication and a large double stranded DNA genome (160 kilobases). Multiple lines of evidence indicate that myxoma, like all poxviruses, encodes multiple gene products whose function is to permit the spread and propagation of the virus in a variety of host tissues. Some of these viral proteins specifically counteract or subvert the development of the host inflammatory response and acquired cellular immunity, and poxviruses in general have been a rich source of such immunomodulatory proteins (Turner, P. C., and Moyer, R. W., Cur. Top. Microbiol. Imm., 163:125–152, 1990; Buller, R. M. L., and Palumbo, G. J., Micro. Dev., 55:80–122, 1991; Smith, G. L., J., Gen. Virol., 94:1725–1740, 1993; McFadden, G., (Ed.), "Viroceptors, virokines and related immune modulators encoded by DNA viruses", R. G. Landes Co., Austin Tex., 1995).

Examples of such immunomodulatory gene products include myxoma growth factor (MGF), which stimulates neighboring cells in a paracrine-like fashion via the cellular epidermal growth factor receptor (Upton, et al., J. Virol., 61:1271–1275, 1987; Opgenorth, et al., Virol., 186:185–191, 1992; Opgenorth, et al., Virol., 192:701–708, 1992; Opgenorth, et al., J. Virol., 66:4720–4731, 1992); Serp 1, a secreted glycoprotein with serine protease inhibitor activity, that prevents development of the early inflammatory response (Upton, et al., Virol., 179:628–631, 1990; Lomas, et al., JBC, 268:516–521, 1993; Macen, et al., Virol., 195:348–363, 1993); T2, a secreted viral homologue of the cellular tumor necrosis factor (TNF) receptor superfamily, that binds and inhibits rabbit TNF (Smith, et al., BBRC, 176:335–342, 1991; Schreiber, M. and McFadden, G., supra, 1994; Upton, et al., supra, 1991); T7, a secreted viral homologue of the cellular interferon-γ receptor, that binds and inhibits rabbit interferon-γ (Upton, et al., Science, 258:1369, 1992; Upton and McFadden, Methods in Molecular Genetics, 4:383, 1994; Mossman, et al., In: "Viroceptors, virokines and related immune modulators" p. 41–54 Ed. McFadden, R. G. Landers, Co., 199.5); and M11L, a surface receptor-like protein that interferes within the inflammatory response by an unknown mechanism (Opgenorth, et al., supra; Graham, et al., Virol, 191:112–124, 1992);

Immunomodulatory proteins also include chemotactic cytokines, called "chemokines". Chemokines are small molecular weight immune ligands which are chemoattractants for leukocytes, such as especially neutrophils, basophils, monocytes and T cells. There are two major classes of chemokines which both contain four conserved cysteine residues which form disulfide bonds in the tertiary structure of the proteins. The α class is designated C-X-C (where X is any amino acid), which includes Il-8, CTAP-III, gro/MGSA and ENA-78; and the β class, designated C-C, which includes MCP-1, MIP-1α and β, and regulated on activation, normal T expressed and secreted protein (RANTES). The designations of the classes are according to whether an intervening residue spaces the first two cysteines in the motif. In general, most C-X-C chemokines are chemoattractants for neutrophils but not monocytes, whereas C-C chemokines appear to attract monocytes but not neutrophils. Recently, a third group of chemokines, the "C" group, was designated by the discovery of a new protein called lymphotactin (Kelner, et al., Science, 266:1395–1933, 1994). The chemokine family is believed to be critically important in the infiltration of lymphocytes and monocytes into sites of inflammation.

It is highly likely that more immunomodulatory viral genes remain to be discovered. Not only will these and related gene products provide useful tools to dissect out the different arms of the host antiviral defense mechanisms, but they may also provide new probes to identify novel elements of the cellular immune repertoire and new classes of drugs to suppress inflammation and dysregulation of the immune system.

SUMMARY OF THE INVENTION

The present invention describes a new family of soluble virus-specific inhibitors for a class of cytokines which are involved in leukocyte chemotaxis and are collectively referred to as "chemokines". These proteins are designated type 2 chemokine binding proteins (type-2 CBP) and are a family of poxviruses proteins related to the T1 protein encoded by Shope fibroma virus and myxoma virus (SFV-T1). The type-2 CBP and related functionally homologues are useful for treatment of a variety of inflammatory disorders in which excessive influx of leukocytes is associated with the pathogenic process.

BRIEF DESCRIPTION OF THE DRAWINGS

FIG. 1 shows the sequence alignment of the known members of the type-2 CBP family of the poxvirus proteins that bind to chemotactic cytokines (chemokines) (SEQ ID NOs: 2–8). The RPV 35 KDa sequence is incomplete.

FIG. 2 shows the nucleotide sequence of the T1 gene of myxoma, which expresses a type-2 CBP. The boxed nucleotide triplet is the stop codon for the adjacent T2 gene (TNF-receptor homolog), the arrow denotes the predicted signal peptide cleavage site, and the underlined amino acids are the two predicted N-glycosylation sites for the T1 protein (SEQ ID NO: 1 and SEQ ID NO:2).

FIG. 5 shows the nucleotide sequence and amino acid sequence of the T1 gene of myxoma, which expresses a type-2 CBP, after a second sequencing of the gene (SEQ ID NO: 9 and SEQ ID NO: 10). The second sequencing revealed a single amino acid change at position 34, from an alanine to a valine.

DETAILED DESCRIPTION OF THE INVENTION

Figure 3A:
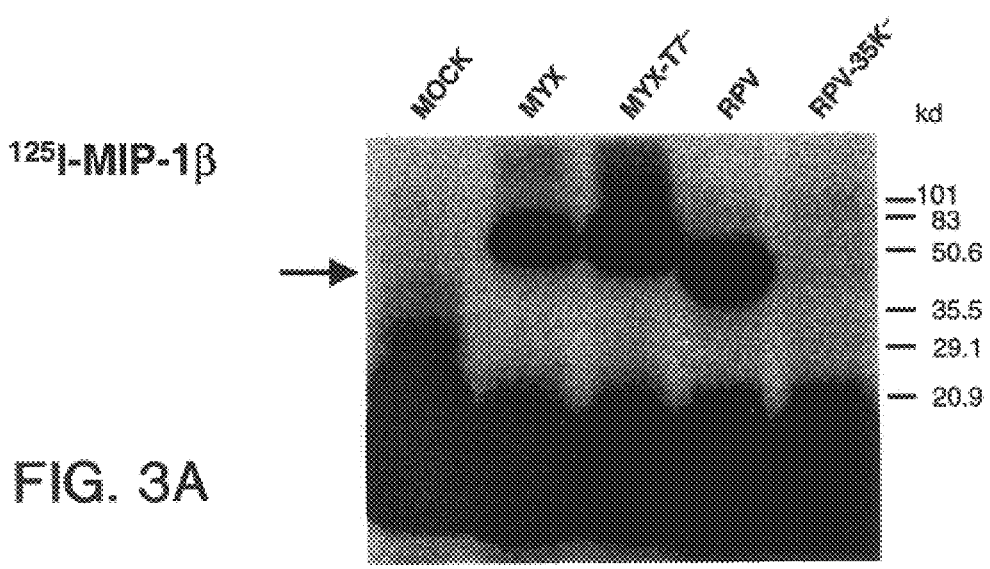
FIG. 3 shows that the 35 KDa protein of rabbit poxvirus (RPV), one of the members of the type-2 CBP family, binds members of the C-C family of chemokines (MIP-1beta, upper panel), and the C-X-C family (11-8, middle panel). In the upper two panels, the radiolabelled ligands are cross-linked to viral proteins secreted from control infected BGMK cells (MOCK), or cells infected with myxoma (MYX), a T7-deletion mutant of myxoma (MYX-T7–), rabbit poxvirus (RPV), and a 35 KDa-deletion mutant of RPV (RPV-35K–). The cross-linked complexes between the ligand and the viral proteins are indicated with the arrows. Although the myxoma type-1 CBP protein (T7) also binds chemokines, the type-2 CBP protein (T1) is virtually the same size (ca 35 KDa), as shown in the bottom panel. Both T1 (type 2) and T7 (type 1) proteins of myxoma thus bind chemokines, but only the 35 KDa protein of RPV (type 2) has this activity.
Figure 3B:
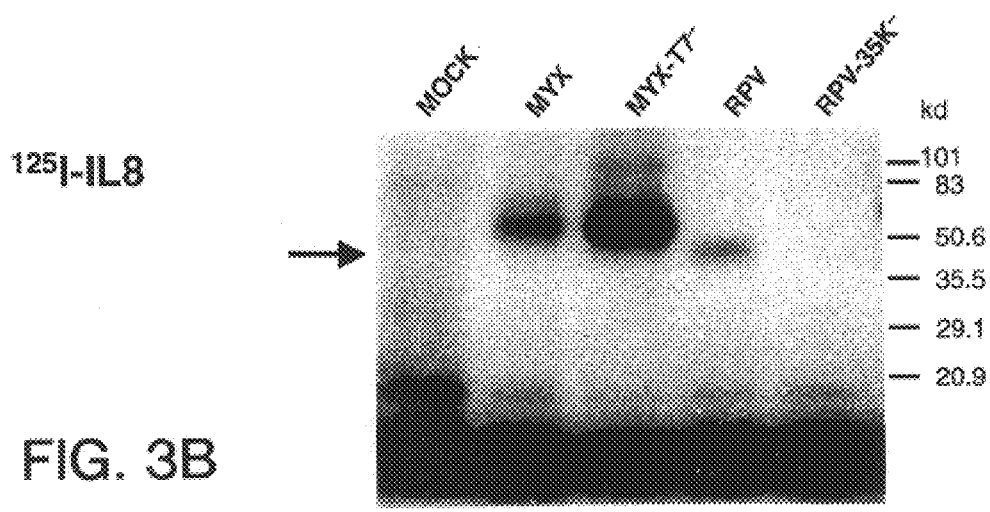
Figure 3C:
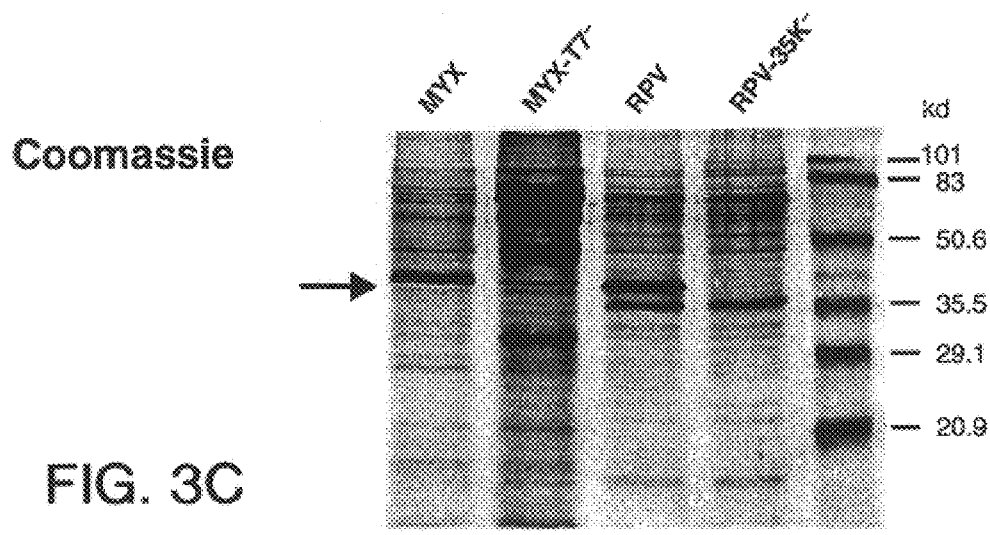
Figure 4:
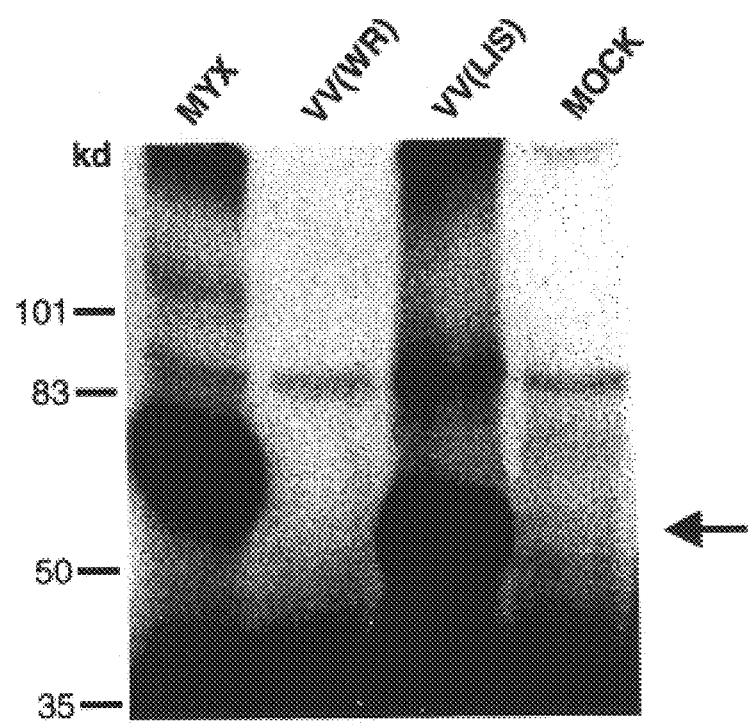
FIG. 4 shows that the 35 KDa secreted protein from vaccinia (strain Lister), but which is missing from strain WR, binds the chemokine MIP-1β similarly to the 35 KDa secreted protein of RPV. The arrow marks the complex between MIP-1B and the 35 KDa protein secreted from BGMK cells infected with vaccinia strain Lister, but not strain WR.

The findings of the present invention provide an important new source of anti-immune proteins which have the potential to treat a wide range of immunopathological conditions associated with the trafficking of lymphocytes and monocytes from the circulation to tissue sites during inflammation and immune responses to damage, infection and various disease states.

The cloned and sequenced type-2 CBP genes are not secreted homologues of the known chemokine receptors, which all possess seven membrane-spanning domains (called "serpentines") as described in recent reviews (Kelvin, D. J., et al., *J. Leukocyte Biol.*, 54:604–612, 1993; Murphy, P. M., *Ann. Rev. Imm.*, 12:593–633, 1994; Horuk, R., *Imm. Today.*, 15:169–174, 1994; and Horuk, R., *Trends in Pharm. Sci.*, 15:159–165, 1994). Although some DNA viruses do encode homologues of such serpentine receptors (Ahuja, S. K., et al., *Imm. Today,* 15:281–287, 1994), including at least one gene candidate in a poxvirus (Massung, R. F., et al., *Virology,* 197:511–528, 1994), the type-2 CBP of the present invention is not a member of this particular receptor family.

The exemplary type-2 chemokine binding protein (type-2 CBP) of the invention is one of the secreted proteins from cells infected with Shope fibroma virus and is encoded by the T1 open reading frame (Upton, et al., *Virology,* 160:20–30, 1987; and GenBank Accession No: P25946). This protein has significant sequence similarity to the secreted 35 kDa proteins of vaccinia (strains Copenhagen and Lister) and rabbit poxvirus. Further, the type-2 CBP proteins are distinct from the myxoma M-T7 protein which specifically binds rabbit IFN-γ, but not mouse or human IFN-γ (Mossman, et al., *J. Biol. Chem.,* 270:3031–3038, 1995) but which also binds chemokines and is designated as a type-1 chemokine binding protein (previously denoted chemokine binding protein-1 (CBP-1)).

The term "chemokine binding protein" refers to a protein which binds to and inhibits one or more chemokines. A "chemokine" is a class of cytokines which are responsible for leukocyte chemotaxis. The α class of chemokines is designated C-X-C (where X is any amino acid), which includes interleukin-8 (Il-8), connective tissue activating protein III (CTAP-III), melanocyte growth stimulatory activity (MGSA) gro/MGSA, IFN-γ inducible protein (IP-10), neutrophil activating peptide 2 (NAP2), β-thromboglobulin and epithelial-derived neutrophil attractant-78 (ENA-78); and the β class, designated C-C, which includes T-cell activation gene-3 (TCA-3), monocyte chemotactic proteins (MCP-1, 2, and 3), macrophage inflammatory proteins (MIP-1α and β), and regulated on activation, normal T expressed and secreted protein (RANTES).

Other chemokines can be detected by methods commonly used in the art. For example, a molecule may be tested using the Boyden chamber, which is the preferred microchemotaxis assay sytem for in vitro investigation of chemoattractant substances. A series of wells is formed into a plexiglass block, each well consisting of two chambers, upper and lower, which are separated by any one of several types of porous filters, such as nitrocellulose and polycarbonate, for example. The cell of interest, for example peripheral blood mononuclear cells (PBMC) are added to the top chamber of each well and the test substance, e.g., the chemoattractant, is added to the bottom chamber. If the cells in the top chamber are attracted to the substance in the bottom chamber, they will migrate along the theoretical concentration gradient which exists in solution and crawl through the pores of the filter and adhere to the bottom side of that filter.

Polypeptides suspected of being members of the chemokine family can now be screened using the CBP of the invention. Therefore, in one embodiment, the invention provides a method for screening and identifying novel chemokines comprising contacting free or matrix-bound CBP of the invention with a composition suspected of containing one or more chemokines and detecting binding of the CBP to the composition.

If desirable, various labels can be used as means for detecting binding of CBP to a chemokine. Chemokines or the CBP can be directly or indirectly detectably labeled, for example, with a radioiscope, a fluorescent compound, a bioluminescent compound, a chemiluminescent compound, a metal chelator or an enzyme. Those of ordinary skill in the art will know of other suitable labels or will be able to ascertain such, using routine experimentation.

In one embodiment, the invention provides a method for treating an immunopathological disorder in a subject comprising administering to the subject a therapeutically effective amount of an anti-inflammatory protein characterized as having a molecular weight of approximately 30–40 kD, depending on the extent of glycosylations as determined by reduced SDS-PAGE, having amino acid sequence homology with the SFV T1 or RPV 35 kDa homolog and having the property of being secreted from infected cells. The term "anti-inflammatory" refers to reduction or suppression of an inflammatory response.

The glycosylated and secreted form of the type-2 CBP of the invention has an apparent molecular weight of approximately 35–40 kD as determined under reducing conditions on an SDS-PAGE. In addition, the protein has homology with the SFV T1 and RPV 35 kDa secreted proteins. The term "homology" refers to the extent of identity between the type-2 CBP and other family members at the amino acid level. Preferably, the type-2 CBP has between 50–95% amino acid sequence homology with the SFV T1 protein. The homology requirement is not stringent, however, the type-2 CBP must retain the biological function of interacting with human chemokines. In other words, the homology is sufficient as long as the type-2 CBP binds and inhibits chemokines.

The invention includes a functional polypeptide, type-2 CBP, and functional fragments thereof As used herein, the term "functional polypeptide" refers to a polypeptide which possesses a biological function or activity which is identified through a defined functional assay and which is associated with a particular biologic, morphologic, or phenotypic response. Functional fragments of the type-2 CBP polypeptide, include fragments of type-2 CBP as long as the activity of type-2 CBP remains (e.g., binding to chemokines). Smaller peptides containing the biological activity of type-2 CBP are included in the invention. Such peptides can be assayed for binding to chemokines by methods commonly known to those of skill in the art, including methods described in the EXAMPLES herein. The biological function can vary from a polypeptide fragment as well as an epitope to which an antibody molecule can bind to a large polypeptide which is capable of participating in the characteristic induction or programming of phenotypic changes within a cell. A "functional polynucleotide" denotes a polynucleotide which encodes a functional polypeptide as described herein.

Minor modifications of the type-2 CBP primary amino acid sequence may result in proteins which have substantially equivalent activity as compared to the type-2 CBP polypeptide described herein. Such modifications may be deliberate, as by site-directed mutagenesis, or may be spontaneous. All of the polypeptides produced by these modifications are included herein as long as the activity of type-2 CBP is retained. Further, deletion of one or more amino acids can also result in a modification of the structure of the resultant molecule without significantly altering its activity. This can lead to the development of a smaller active molecule which would have broader utility. For example, it is possible to remove amino or carboxy terminal amino acids which may not be required for type-2 CBP activity.

The type-2 CBP polypeptide of the invention also includes conservative variations of the polypeptide sequence. The term "conservative variation" as used herein denotes the replacement of an amino acid residue by another, biologically similar residue.

Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Examples of viral sources of the type-2 CBP used in the method of the present invention include myxoma virus, vaccinia (strains Lister and Copenhagen), Shope fibroma virus, rabbitpox and other mammalian pox viruses, as long as the type-2 CBP has the biological function of an anti-inflammatory protein characterized as having a molecular weight of approximately 30–40 kD, depending on extent of glycosylation having homology with SFV TI protein homolog, and having the biological function of this family of proteins.

An immunopathological disorder treated by the method of the invention may be associated with production of chemokines and resultant accumulation of reactive leukocytes at afflicted tissues. The method comprises administering to the subject a therapeutically effective amount of type-2 CBP. The term "immunopathological disorder" refers to any disease which involves the immune response or immunity in general. "Therapeutically effective" as used herein, refers to that amount of type-2 CBP that is of sufficient quantity to ameliorate the cause of the immunopathological disorder. "Ameliorate" refers to a lessening of the detrimental effect of the disorder in the patient receiving the therapy. The subject of the invention is preferably a human, however, it can be envisioned that any animal with an immunopathological disorder can be treated by the method of the invention, for example, a SCID mouse grafted with human bone marrow (humanized SCID). Examples of immunopathological disorders which can be treated by the method of the invention include acquired immunodeficiency disorder (AIDS), toxic shock syndrome, allograft rejection, artherosclerotic plaque growth, ultraviolet and radiation responses, and disorders associated with the activation of T cells, B cells, macrophages, and other inflammatory leukocytes during the immune response and the acute phase response and disorders associated with advanced cancer such as tumor necrosis factor-mediated cachexia.

The invention provides a method of treating or ameliorating an immunopathological disorder including endotoxemia or septic shock (sepsis), or one or more of the symptoms of sepsis comprising administering to a subject displaying symptoms of sepsis or at risk for developing sepsis, a therapeutically effective amount of type-2 CBP. The term "ameliorate" refers to a decrease or lessening of the symptoms of the disorder being treated.

A patient who exhibits the symptoms of an immunopathological disorder may be treated with an antibiotic or antiviral agent in addition to the treatment with type-2 CBP. Typical antibiotics include an aminoglycoside, such as gentamycin or a beta-lactam such as penicillin, or cephalosporin. Therefore, a therapeutic method of the invention includes administering a therapeutically effective amount of type-2 CBP substantially simultaneously with administration of a bactericidal amount of an antibiotic or sufficient amount of an anti-viral compound.

The term "bactericidal amount" as used herein refers to an amount sufficient to achieve a bacteria-killing blood concentration in the patient receiving the treatment. The bactericidal amount of antibiotic generally recognized as safe for administration to a human is well known in the art, and as is known in the art, varies with the specific antibiotic and the type of bacterial infection being treated. Preferably, administration of type-2 CBP occurs within about 48 hours and preferably within about 2–8 hours, and most preferably, substantially concurrently with administration of the antibiotic.

Administration of a type-2 CBP in the method of the invention may also be used for ameliorating post-reperfusion injury. When treating arterial thrombosis, induction of r-eperfusion by clot lysing agents such as tissue plasminogen activator (t-PA) is often associated with tissue damage. Such tissue damage is thought to be mediated at least in part by leukocytes including but not limited to polymorphonuclear leukocytes (PMN). Therefore administration of the type-2 CBP would block leukocyte or PMN-endothelial interactions, and thereby diminish or prevent post-reperfusion injury. Administration of type-2 CBP is also useful for prevention of new onset and recurrent atherosclerotic plaque growth after arterial injury. Restenosis and new growth of plaque is believed to be exacerbated by the local inflammatory response to the internal layer of the artery wall.

The method of the invention is also useful for treatment of inflammation due to allergic or autoimmune disorders. Examples of allergic disorders include allergic rhinitis, asthma, atopic dermatitis, and food allergies. Examples of autoimmune disorders, where the immune system attacks the host's own tissues, include, but are not limited to, type 1 insulin-dependent diabetes mellitus, inflammatory bowel disease, dermatitis, meningitis, thrombotic thrombocytopenic purpura, Sjögren's syndrome, encephalitis, uveitis, leukocyte adhesion deficiency, rheumatoid and other forms of immune arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune hemolytic anemia, Hashimoto's thyroiditis, Graves disease, habitual spontaneous abortions, Reynard's syndrome, glomerulonephritis, dermatomyositis, chronic active hepatitis, celiac disease, autoimmune complications of AIDS, atrophic gastritis, ankylosing spondylitis and Addison's disease.

The method is also useful in treating non-malignant or immunological-related cell-proliferative diseases such as psoriasis, pemphigus vulgaris, Behcet's syndrome, acute respiratory distress syndrome (ARDS), ischemic heart disease, atherosclerosis, post-dialysis syndrome, leukemia, acquired immune deficiency syndrome, septic shock and other types of acute inflammation, and lipid histiocytosis. Essentially, any disorder which is etiologically linked to the pro-inflammatory process and cellular infiltration due to chemokine production (e.g., induction of IL-8, MIP-1α or β expression) would be considered susceptible to treatment.

The method of the invention is also useful for the treatment of microbial infections. Many microbes, such as bacteria, rickettsia, various parasites, and viruses, bind to vascular endothelium and leukocytes, and induce an inflammatory reaction resulting in production of interleukins for example. Thus, the type-2 CBP used in the method of the invention may be administered to a patient to prevent inflammation associated with such infections.

The dosage ranges for the administration of the type-2 CBP of the invention are those large enough to produce the desired effect in which the symptoms of the immune response show some degree of suppression. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary from about 10 pg to 100 µg per dosage, in one or more dose administrations daily, for one or several days.

The type-2 CBP is administered by any suitable means, including parenteral, subcutaneous, intrapulmonary, intraareterial, intrarectal, intramuscular, and intranasal administration. Parenteral infusions include intramuscular, intravenous, intraarterial, or intraperitoneal administration. Type-2 CBP may also be administered transdermally in the form of a slow-release subcutaneous implant for example, or orally in the form of capsules, powders or granules. Type-2 CBP can also be administered by inhalation. For example, when used therapeutically for treatment of an inflammatory disorder of the lungs, a preferred route of administration would be by a pulmonary aerosol.

Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient is often mixed with excipients which are pharmaceutically acceptable and compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

The invention also relates to a method for preparing a medicament or pharmaceutical composition comprising the type-2 CBP of the invention, the medicament being used for therapy of an undesirable immune response/inflammatory reaction wherein the immune response results in production of chemokines which bind to the type-2 CBP of the present invention.

The invention provides a pharmaceutical composition comprising at least one dose of an immunotherapeutically effective amount of an anti-inflammatory protein having a molecular weight of approximately 30–40 kD, depending on the extent of glycosylation, having amino acid sequence homology with the myxoma T1 interferon-γ receptor homolog, and having the biological function of the myxoma T1 interferon-γ receptor homolog, in a pharmacological carrier.

The invention provides any pharmaceutical preparations and compositions containing the type-2 CBP of the invention for use in the method of the invention. The form will vary depending upon the route of administration. For example, compositions for injection can be provided in the form of an ampule, each containing a unit dose amount, or in the form of a container containing multiple doses.

Type-2 CBP can be formulated into the therapeutic composition as neutralized pharmaceutically acceptable salt forms. These include the acid addition salts which are formed with inorganic acids such as, for example, hydrochloric or phosphoric acid, or organic acids such as acetic, oxalic, tartaric and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by selecting appropriate macromolecules, for example, polyesters, polyamino acids, polyvinyl pyrrolidone, ethylenevinylacetate, methyl cellulose, carboxymethylcellulose, protamine sulfate, or lactide/glycolide copolymers. The rate of release of the type-2 CBP may be controlled by altering the concentration of the macromolecule.

Another method for controlling the duration of action comprises incorporating the type-2 CBP into particles of a polymeric substance such as polyesters, polyamino acids, hydrogels, polylactide/glycolide copolymers, or ethylenevinylacetate copolymers. Alternatively, it is possible to entrap type-2 CBP in microcapsules prepared, for example, by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The following examples are intended to illustrate but not limit the invention. While they are typical of those that might be used, other procedures known to those skilled in the art may alternatively be used.

EXAMPLE 1

Materials and Methods
Rat Model of Injury Induced Atherosclerosis

Sprague Dawley rats were induced to have balloon angioplasty mediated injury of the right or left iliofemoral artery. A 1.5 mm USCI angioplasty balloon was advanced retrograde into the artery via cut down and arteriotomy under general pentobarbital anesthetic (6.5 mg per 100 g weight by i.m. injection, Somnotrol, MTC Pharmaceuticals, Cambridge, Ontario). 500 pg of CBP (6 rats) or saline (6 rats) was given by intra-arterial injection of the CBP or control solution into the distal lumen of the angioplasty balloon catheter upstream from the site of subsequent balloon mediated damage. The balloon was then inflated to 8 bars pressure for 1.0 minutes. After angioplasty the balloon was deflated and withdrawn and the arteriotomy site closed with local application of n-butyl cyanoacrylate monomer (Nexaband, Veterinary Products Laboratories, Phoenix, Ariz.). Each rat was maintained on a normal rat diet and was followed up for 4 weeks post surgery. At follow up, the rats were sacrificed with 2.0 ml euthanyl per kg and the aorta was harvested for histological examination.

Rabbit Model of Injury Induced Atherosclerosis

Eight cholesterol fed New Zealand white rabbits are treated by balloon angioplasty of the distal abdominal aorta. All rabbits (strain New Zealand white) are fed 2% cholesterol in 10% peanut oil diet for 4 days/week, beginning 2 weeks before balloon injury. A 3–3.5 mm angioplasty balloon catheter ($\geq$1:1 ratio of balloon to aorta diameter) is introduced via femoral arterial cut down following anesthetic (40 mg/kg ketalean, 8 mg/kg xylazene, and 0.5 mg/kg acepromazine by intramuscular injection). The balloon is inflated to 8 bars pressure in the distal abdominal aorta and advanced retrograde to the distal thoracic aorta. The balloon is advanced and withdrawn 3 times under fluoroscopic control in each rabbit to ensure endothelial denudation. Contrast angiograms are recorded prior to and after balloon angioplasty mediated trauma and at 4 weeks follow-up. Heparin (400 units) is given immediately after obtaining femoral access to decrease catheter associated thrombosis.

Purified type-2 CBP, 500 pg per sample, is infused immediately after balloon mediated injury in the distal abdominal aorta of 4 rabbits. A parallel infusion of saline is infused locally into the distal abdominal aorta in 4 rabbits. Each infusate is administered via Wolinsky catheter in a total volume 10 ml diluted in sterile 0.9% saline immediately following balloon mediated injury. All infusions are via a 3.25 mm Wolinsky balloon (inflated to a final pressure of 6±1 bars for 2 minuets) in the abdominal aorta proximal to the iliac bifurcation. The Wolinsky balloon is positioned immediately above the iliac bifurcation under fluoroscopic control such that the perfusion balloon is routinely located from 0.5–2.5 cm above the bifurcation and designated as the primary infusion site. Upstream secondary sites are defined in the region above 2.5 cm proximal to the iliac bifurcation. In all experiments, infusates are administered via Wolinsky catheter in a total volume of 10 ml diluted in sterile 0.9% saline immediately following balloon mediated injury. All infusions are via a 3.25 mm Wolinsky balloon (inflated to a final pressure of 6±1 bars for 2 minutes) in the abdominal aorta proximal to the iliac bifurcation.

Histology and Morphometric Analysis

Histological analysis is performed at the primary site of Wolinsky infusion in the distal abdominal aorta (rabbits) or upper iliofemoral arterial branches (rat) representing the primary infusion site as defined by the original positioning of the perfusion balloon. In rabbits, internal control sections are taken from a downstream, non-infused site near the iliac bifurcation (0.5 cm above the bifurcation to 0.5 cm below the bifurcation) and in upstream, non-infused site (the upper abdominal aorta, 2.5 cm–3.5 cm above the iliac bifurcation). The area from 1.5–2.5 cm above the iliac bifurcation is considered a border zone with potentially variable infusion doses due to balloon placement and is therefore not included in this analysis. In rats the primary balloon sites for both T-1 treated and saline infused rats were used for histological assessment. Hematoxylin and eosin staining of formalin fixed specimens was performed as previously described. Briefly, each specimen was fixed in 10% (v/v) sodium phosphate buffered formalin, processed, impregnated, embedded in paraffin and cut into 5 μm sections by microtome. Sections from each specimen (a minimum of 2 sections per site) were then stained with hematoxylin and eosin and examined by light microscopy.

EXAMPLE 2

Binding of Cytokines to a Novel Viral Protein

Briefly, a variety of human cytokines were radiolabeled with $^{125}$I, exposed to the secreted proteins harvested from control or poxvirus-infected BGMK cells, cross-linked, and then analyzed by SDS-PAGE for novel cytokine/protein complexes.

The cross-linking assay uncovered what was clearly a novel viral-specific protein that bound to each of the human chemokines that was tested: IL-8 and MIP-1β (FIG. 2). FIG. 2 (upper two panels) shows gel mobility shift assays using iodinated ligands and tissue culture supernatants. Tissue culture supernatants (Sups) were prepared as follows: BGMK (Baby Green Monkey Kidney Cells) left untreated (mock) or were infected with Myxoma (MYX), T7-deletion mutant of myxoma (myx-T7⁻), rabbit pox (RPV) or a 35 kDa-deletion of RPV at a multiplicity of infection (MOI) of 3. Secreted proteins were prepared by washing the monolayer three times with PBS and replenishing it with serum free medium at 4 h post infection; these supernatants were then collected at 18 h post infection (L). Mock supernatants were prepared in the same way in the absence of virus. Supernatants were concentrated approximately 15 fold using Amicon concentrators. The human chemokines IL-8 and MIP-1β were labeled with $^{125}$I using iodobeads (Pierce) according to the manufacturer's protocols.

The gel mobility shift assays were performed as follows: 5 μl of iodinated ligand was mixed with 10 μl SUP and allowed to sit at room temperature for 2 hours. then 2 μl of the chemical cross linking reagent 1-ethyl-3-(3-dimethylaminopropyl)-carbodiimide (EDC) (200 mM in 100 mM potassium phosphate, pH 7.5) was added for 15 minutes, followed by an additional 2 μl for 15 minutes. The reaction was then quenched by the addition of 2 μl of Tris-HCl (1.0M, pH 7.5). The resulting mixture was analyzed using SDS-PAGE and autoradiography. The arrows indicate the shifted complexes. The bottom panel indicates the Coomassie stained gels, showing the loss of the T7 protein in the myx-T7⁻ infection and the loss of the 35 KDa protein in the RPV-35k⁻ infection.

EXAMPLE 3

Analysis of the Efficacy of Type-2 CNP (T1) as an Anti-restenosis Protein as Shown in Angioplasty Balloon Mediated Injury in Rat Femoral Arteries Inflammation is associated with accelerated atherosclerotic plaque development in the arterial wall. There is a high rate of plaque recurrence, or restenosis, after the use of balloon angioplasty and other related angioplasty devices designed to open occluded arteries. Accelerated atherosclerotic plaque growth also has been reported under conditions leading to arterial injury, viral infections, vasculitis, homocystinuria, diabetes melitis, hypertension, hyperlipideuria, smoking and immune complex generated disorders. The larger DNA viruses have evolved mechanisms, such as anti-inflammatory proteins, that allow the virus to proliferate in the host with decreased inhibition by the host immune and inflammatory defense mechanisms. Type-2 CBP (T-1) was tested as a potential therapeutic agent for the prevention of plaque growth after angioplasty. Type-2 CBP is believed to act as both an interferon gamma receptor homologue and as a chemokine inhibitor. Type-2 CBP was tested in animal models of injury induced atherosclerosis and the results showed a significant decrease in plaque formation 4 weeks after infusion. The 35 KDa protein, a Type-2 CBP isolated from Vaccinia virus, significantly decreased intimal hyperplasia (atherosclerotic plaque growth) after balloon angioplasty injury after a single intravenous injection (Table 1). This shows that type-2 CBP can be used as an anti-inflammatory agent for treatment of or prevention of immune based disorders.

10 Sprague Dawley rats were induced to have balloon injury of the right iliofemoral artery under general anesthesia. A 1.5 mm angioplasty balloon was introduced via femoral arterial cutdown and the distal tip of the balloon was advanced to the iliac bifurcation. Immediately prior to inflating the balloon, 1.0 ml of either saline (5 rats) or increasing concentrations of purified vaccinia 35K protein, at 50 pg (5 rats), was injected into the artery. The angioplasty balloon was then inflated to 6–8 atm for 2 minutes, deflated and removed. The femoral artery was sealed with nexaband at the puncture site after removal of the catheter. The rats were allowed to recover and were monitored for 4 weeks. At 4 weeks the rats were sacrificed and the arteries harvested for histological assessment. Intimal area was measured by morphometric analysis. A significant decrease in intimal hyperplasia (plaque area) was detected after 35 KDa protein infusion in comparison with the control saline infusions (p<0.0089) (Table 1).

TABLE 1

| Dose 35KDa | mean Plaque area mm² | S.E. | p value (t test) |
|---|---|---|---|
| 0 | 0.055 | 0.012 | NS |
| 50pg | 0.014 | 0.011 | 0.0089 |

EXAMPLE 4

CBP-II Inhibits Chemokine Binding to Cellular Receptors of Human Monocytes

The inhibition of binding of human MIP-1α to surface receptor in primary human monocytes and THP-1 cells by 35 KDa protein from vaccinia (strain Lister) (Table 2) and M-T1 (Table 3), respectively, was demonstrated according to the following protocol. (Note: experiment 3 in Tables 1 and 2 used THP-1 cells, all other results were obtained from primary monocytes.)

Radiolabeled $^{125}$I MIP-1α (25 μCi/ml) was obtained and an appropriate volume of radiolabeled (hot) MIP-1α was added such that each tube contains 50,000 cpm. As a control, unlabeled (cold) MIP-1α was added (400 ng) along with the hot MIP-1α to demonstrate background binding. To measure the inhibitory properties of 35 KDa M-T1 (CBP-2) and M-T7 (CBP-1), varying doses of the inhibitor were added with the radiolabeled ligand and the samples were incubated at 37° C. (5% CO₂) for 30 minutes. Primary monocytes isolated from human blood and separated on a Percoll gradient were diluted in RPMI 1640 containing 1% BSA to a concentration of 1×10⁷ cells/ml, and 200 μl of these cells were added to each reaction. Similar concentrations were used for THP-1 cells (monocytic cell line). The sample tubes were rotated for 1 hour at room temperature, whereupon the cells were spun down at 13,000 rpm for 5 minutes. The supernatants were removed, and the cells washed with 800 μl of 10% sucrose solution. The cells were again spun at 13,000 rpm for 10 minutes, and the supernatants removed. The radioactivity from the pellets was then measured using a gamma counter. As a second set of controls, the binding properties of H³-fMLP to its cellular receptor was also tested in the presence of the inhibitors (Table 4). The above protocol was followed, with the exception that a uniform volume of 1 μl was distributed to each tube, which resulted in counts of approximately 180,000 cpm per tube. Note that 35 KDa and M-T1 both quantitatively blocked binding of the chemokine to the cellular receptors of MIP-1α.

TABLE 2

Surface Bound MIP-1α

| | Molar excess of 35KDa protein | | | | | | | | Excess unlabeled MIP-1α | labeled |
|---|---|---|---|---|---|---|---|---|---|---|
| Exp. | 1600 | 800 | 400 | 200 | 50 | 40 | 4 | 2 | 6500X | MIP-1α |
| 1 | 80 | 77 | 107 | 144 | 1280 | — | — | — | 470 | 4705 |
| 2 | — | — | — | 88 | — | 2342 | 10688 | 9113 | 410 | 7708 |
| 3 | 55 | — | — | — | — | — | — | — | 1038 | 9944 |

Note:
Experiment 3 used THP-1 cells; Experiment 1 and 2 used primary monocytes.

TABLE 3

Surface Bound MIP-1α

| Exp. | 200× Molar excess M-T1 | 200× Molar excess M-T7 | 6500× Molar excess unlabeled MIP-1α | Labeled MIP-1α |
|---|---|---|---|---|
| 1 | 978 | 10171 | 444 | 12206 |

TABLE 4

Surface Bound fMLP

| Exp. | Labeled fMLP | 1 × 10$^6$ M unlabeled fMLP | 35KDa (400 ng) |
|---|---|---|---|
| 1 | 374 | 132 | 507 |

Although the invention has been described with reference to the presently preferred embodiment, it should be understood that various modifications can be made without departing from the spirit of the invention. Accordingly, the invention is limited only by the following claims.

---

What is claimed is:

1. An isolated type-2 chemokine binding protein, wherein the protein comprises an amino acid sequence as set forth in SEQ ID NO: 2 or 10, or a conservative substitution of a single amino acid residue at position 34 of SEQ ID NO: 2 or 10, wherein said type-2 chemokine binding protein binds an α or β chemokine.

2. The composition of claim 1, wherein the protein binds a class α chemokine.

3. The composition of claim 1, wherein the protein binds a class β chemokine.

4. The composition of claim 2 or 3, wherein the chemokine is selected from the group consisting of CTAP-III, gro/MGSA, ENA-78, MCP-1, interleukin-8, RANTES, MIP-1α, and MIP-1β, PF-4, IP-10, and NAP-2.

5. A pharmaceutical composition comprising the protein of claim 1.

* * * * *